US010458885B2

(12) United States Patent
Shaw et al.

(10) Patent No.: US 10,458,885 B2
(45) Date of Patent: Oct. 29, 2019

(54) RAPID DESORBER HEATING AND COOLING FOR TRACE DETECTION

(71) Applicant: Rapiscan Systems, Inc., Torrance, CA (US)

(72) Inventors: Bradley Douglas Shaw, Plaistow, NH (US); Dung Lu, Maiden, MA (US); Stephen L. Crook, Reading, MA (US); Karl Goedecke, Everett, MA (US); Hanh T. Lai, Arlington, MA (US); Vladimir Romanov, Pelham, NH (US)

(73) Assignee: Rapiscan Systems, Inc., Torrance, CA (US)

( * ) Notice: Subject to any disclaimer, the term of this patent is extended or adjusted under 35 U.S.C. 154(b) by 148 days.

(21) Appl. No.: 15/476,616

(22) Filed: Mar. 31, 2017

(65) Prior Publication Data

US 2018/0284081 A1 Oct. 4, 2018

(51) Int. Cl.

| | |
|---|---|
| ***G01N 30/54*** | (2006.01) |
| ***G01N 1/02*** | (2006.01) |
| ***B01L 7/00*** | (2006.01) |
| ***G01N 1/40*** | (2006.01) |

(52) U.S. Cl.

CPC .................. *G01N 1/02* (2013.01); *B01L 7/00* (2013.01); *G01N 1/405* (2013.01); *B01L 2300/0663* (2013.01); *B01L 2300/10* (2013.01); *B01L 2300/185* (2013.01); *B01L 2300/1844* (2013.01); *B01L 2300/1894* (2013.01)

(58) Field of Classification Search

CPC .. H01J 49/049; H01J 49/0468; H01J 49/0481; G01N 2030/8476; G01N 2030/128; G01N 2030/008

See application file for complete search history.

(56) References Cited

U.S. PATENT DOCUMENTS

| | | | | |
|---|---|---|---|---|
| 3,067,560 A | | 12/1962 | Albert | |
| 3,705,480 A | | 12/1972 | Wireman | |
| 4,909,090 A | * | 3/1990 | McGown | G01N 1/2214 73/863.12 |
| 5,123,274 A | * | 6/1992 | Carroll | G01N 1/02 436/156 |
| 5,313,061 A | * | 5/1994 | Drew | B01D 59/44 250/281 |
| 5,350,442 A | | 9/1994 | Thelen | |
| 5,465,607 A | * | 11/1995 | Corrigan | G01N 1/2214 73/23.36 |
| 5,491,337 A | | 2/1996 | Jenkins | |

(Continued)

FOREIGN PATENT DOCUMENTS

| | | |
|---|---|---|
| AT | 303589 T | 9/2005 |
| AT | 480769 T | 9/2010 |

(Continued)

OTHER PUBLICATIONS

International Search Report for PCT/US2018/024848, dated Jul. 2, 2018.

*Primary Examiner* — Harshad R Patel
*Assistant Examiner* — Tran M. Tran
(74) *Attorney, Agent, or Firm* — Novel IP

(57) ABSTRACT

A desorber for a trace detection system. The desorber includes an inlet configured to receive a sample, a heating element configured to generate a vapor from the sample, and an active cooling element configured to cool the desorber.

13 Claims, 7 Drawing Sheets

(56) References Cited

U.S. PATENT DOCUMENTS 5,554,846 A 9/1996 Regiec
5,588,988 A 12/1996 Gerstel et al.
5,970,804 A * 10/1999 Robbat, Jr. ............ G01N 1/405 73/23.41
6,211,516 B1 * 4/2001 Syage .................. H01J 49/107 250/288
6,326,615 B1 12/2001 Syage
6,329,653 B1 12/2001 Syage
6,630,664 B1 10/2003 Syage
6,642,513 B1 11/2003 Jenkins
6,690,005 B2 2/2004 Jenkins
6,708,572 B2 3/2004 Jenkins
6,737,642 B2 5/2004 Syage
6,765,198 B2 7/2004 Jenkins
6,815,670 B2 * 11/2004 Jenkins .................. B01D 53/30 73/863.12
6,831,273 B2 12/2004 Jenkins
6,840,120 B2 * 1/2005 Sakairi ..................... G01N 1/22 73/863.21
6,840,122 B1 1/2005 Jenkins
6,884,997 B2 * 4/2005 Kashima ............... H01J 49/049 250/281
7,002,145 B2 * 2/2006 Ishikawa .............. G01N 1/2214 250/288
7,041,971 B2 * 5/2006 Fukano .............. G01N 33/0044 250/281
7,047,829 B2 * 5/2006 Napoli ................. G01N 27/622 73/863.12
7,109,476 B2 9/2006 Hanold
7,119,342 B2 10/2006 Syage
7,141,786 B2 11/2006 McGann
7,161,144 B2 1/2007 Syage
7,196,325 B2 3/2007 Syage
7,244,288 B2 * 7/2007 Belyakov ............. G01N 1/2214 95/148
7,253,727 B2 8/2007 Jenkins
7,299,710 B2 11/2007 Syage
7,320,725 B2 1/2008 Arno
7,338,638 B2 3/2008 McGann
7,361,206 B1 4/2008 Jahn
7,361,208 B2 * 4/2008 Botelho ................. G01N 30/30 73/23.25
7,401,498 B2 7/2008 Syage
7,448,248 B2 11/2008 Carey
7,456,393 B2 11/2008 Napoli
7,528,367 B2 5/2009 Haigh
7,541,577 B2 6/2009 Davenport
7,594,422 B2 9/2009 Perry
7,594,447 B2 * 9/2009 Napoli ................. G01N 27/622 73/864.71
7,663,099 B2 2/2010 Reda
7,721,588 B2 5/2010 Perry
7,856,898 B2 12/2010 Carey
7,880,137 B2 2/2011 McGann
7,884,320 B2 2/2011 Landgraf
8,161,830 B2 * 4/2012 Boudries ................ G01N 1/405 73/863.12
8,186,234 B2 5/2012 Syage
8,288,735 B2 10/2012 Syage
8,314,383 B2 * 11/2012 Wu ....................... H01J 49/004 250/281
8,402,842 B2 3/2013 Syage
8,434,375 B1 5/2013 Syage
8,448,532 B2 * 5/2013 Martin ................... G01N 1/405 73/863.12
8,614,582 B2 12/2013 Syage
8,686,355 B2 * 4/2014 Patterson ............. G01N 1/2205 250/282
8,723,111 B2 5/2014 Syage
8,752,411 B2 6/2014 Chiarugi
8,756,975 B2 * 6/2014 Wu .......................... G01N 1/14 73/31.05
8,857,278 B2 * 10/2014 Syage .................. G01N 1/2205 73/29.05
8,866,073 B2 10/2014 Goedecke
8,952,327 B2 * 2/2015 Patterson ............. G01N 1/2205 250/281
9,048,076 B2 * 6/2015 Stott ................... H01J 49/0459
9,091,467 B2 * 7/2015 Shreve .................... F25B 21/02
9,134,208 B2 * 9/2015 Hendrikse ............. H01J 49/049
9,147,565 B1 9/2015 Goedecke
9,157,842 B1 10/2015 Ancona et al.
9,354,153 B2 * 5/2016 Syage .................. G01N 1/2208
9,482,655 B2 11/2016 Vilkov
9,528,969 B2 * 12/2016 Shaw ................ G01N 33/0011
9,558,924 B2 1/2017 Syage
9,683,981 B1 * 6/2017 Vilkov ................ G01N 33/227
9,689,847 B2 * 6/2017 Matsuoka .............. G01N 30/54
9,689,857 B1 * 6/2017 Vilkov ................ G01N 33/227
9,726,655 B2 8/2017 Syage
9,766,218 B2 * 9/2017 Lai .......................... G01N 1/44
9,789,434 B1 10/2017 Lai
9,831,077 B2 * 11/2017 Akiyama ............ H01J 49/0422
9,870,904 B2 * 1/2018 Covey ................... H01J 49/167
9,899,198 B2 * 2/2018 Akiyama ............ H01J 49/0009
2003/0164091 A1 9/2003 Hill
2007/0071646 A1 * 3/2007 Schoen .................. H01J 49/02 422/68.1
2009/0090196 A1 4/2009 Clark
2009/0152458 A1 6/2009 Vilkov
2010/0028212 A1 2/2010 He
2010/0126284 A1 5/2010 Boudries
2010/0236341 A1 9/2010 Martin et al.
2011/0210244 A1 9/2011 Wu
2012/0037797 A1 2/2012 Li
2015/0249001 A1 9/2015 Piper
2016/0103102 A1 4/2016 Alborn et al.
2016/0282304 A1 9/2016 Vilkov
2017/0103880 A1 4/2017 Syage
2017/0213715 A1 7/2017 Davila
2017/0261483 A1 9/2017 Vilkov
2017/0261484 A1 9/2017 Vilkov
2017/0284977 A1 10/2017 Rogers
2017/0309463 A1 10/2017 Vilkov
2018/0158665 A1 6/2018 Eiceman
2018/0164189 A1 6/2018 Bilodeau
2018/0172635 A1 6/2018 Lai
2018/0172650 A1 6/2018 Platow
2018/0182603 A1 6/2018 Schmidt
2018/0182604 A1 6/2018 Lai
2018/0283993 A1 * 10/2018 Shaw ...................... G01N 1/02
2018/0284081 A1 10/2018 Shaw
2018/0356320 A1 12/2018 Romanov
2019/0011421 A1 1/2019 Rogers

FOREIGN PATENT DOCUMENTS

CA 2012030 A1 9/1991
CA 2153371 C 3/1999
CA 2436256 C 6/2007
CA 2382823 C 11/2007
CA 2362449 C 10/2008
CA 2411532 C 4/2010
CA 2285153 C 5/2010
CA 2479875 C 2/2011
CA 2538709 C 2/2013
CA 2790430 A1 3/2013
CA 2807894 A1 9/2013
CA 2620405 C 7/2014
CA 2548177 C 9/2014
CA 2844222 A1 9/2014
CA 2845959 A1 9/2014
CA 2688352 C 6/2015
CA 2644937 C 11/2015
CA 2904479 A1 3/2016
CA 2910780 A1 4/2016
CA 2913931 A1 6/2016
CA 2915785 A1 6/2016
CA 2924580 A1 9/2016
CA 2647651 C 11/2016
CA 2738053 C 5/2017

(56) References Cited

FOREIGN PATENT DOCUMENTS

| | | | |
|---|---|---|---|
| CA | 2959791 | A1 | 9/2017 |
| CA | 2959796 | A1 | 9/2017 |
| CA | 2962154 | A1 | 9/2017 |
| CA | 2964147 | A1 | 10/2017 |
| CN | 100445767 | C | 12/2008 |
| CN | 103308590 | A | 9/2013 |
| CN | 105738461 | A | 7/2016 |
| CN | 107037114 | A | 8/2017 |
| CN | 107167334 | A | 9/2017 |
| CN | 107167335 | A | 9/2017 |
| CN | 107271254 | A | 10/2017 |
| DE | 69528418 | T2 | 1/2003 |
| DE | 69926965 | T2 | 6/2006 |
| EP | 692712 | A | 11/1930 |
| EP | 1048540 | A1 | 11/2000 |
| EP | 2368102 | A2 | 9/2011 |
| EP | 2637013 | A2 | 9/2013 |
| EP | 2778650 | A2 | 9/2014 |
| EP | 2778669 | A1 | 9/2014 |
| EP | 2884254 | A1 | 6/2015 |
| EP | 3015858 | A1 | 5/2016 |
| EP | 3032570 | A2 | 6/2016 |
| EP | 3040717 | A1 | 7/2016 |
| EP | 2536076 | A | 9/2016 |
| EP | 1938078 | B1 | 3/2017 |
| EP | 1297554 | B1 | 4/2017 |
| EP | 3182111 | A1 | 6/2017 |
| ES | 2183855 | | 4/2003 |
| GB | 992782 | A | 5/1965 |
| GB | 2496286 | A | 5/2013 |
| JP | 3045655 | B2 | 5/2000 |
| JP | 2006064325 | | 3/2006 |
| WO | 0209847 | A2 | 2/2002 |

* cited by examiner

RAPID DESORBER HEATING AND COOLING FOR TRACE DETECTION

BACKGROUND

The field of the disclosure relates generally to trace detection systems and, more particularly, to a rapid-cooled desorber of a trace detection system.

Various technologies exist for detection of certain substances of interest, such as explosives and illicit drugs. Some trace detection technologies use spectrometric analysis of ions formed by ionization of vapors of substances of interest. Spectrometric analysis includes ion mobility spectrometry and mass spectrometry, for example, both of which are common in trace detection.

Trace detection systems analyze a sample to screen for a substance. The sample may be introduced to the system at an inlet, such as an inlet of a desorber, where the sample is rapidly heated to a desired temperature by a heating element to vaporize the sample. The vapor is then transferred to an analysis device or a detector for spectrometric analysis where it is screened for the substance of interest. When the desorber is cooled to a desired temperature, the trace detection system is ready for a subsequent sample to be introduced at the inlet for analysis.

BRIEF DESCRIPTION

In one aspect, a desorber is provided. The desorber includes an inlet, a heating element, and an active cooling element. The inlet is configured to receive a sample. The heating element is configured to generate a vapor from the sample. The active cooling element is configured to cool the desorber.

In another aspect, a method of operating a trace detection system for detecting a substance of interest within a sample is provided. The method includes receiving a first sample at an inlet of a desorber. The method includes heating, by a heating element, the desorber to a first temperature to release a vapor from the first sample. The method includes transferring the vapor from the desorber to an analysis device configured to screen the vapor for the substance of interest. The method includes cooling the desorber to at least a second temperature. The method includes receiving a second sample at the inlet of the desorber.

In yet another aspect, a system for detecting a substance of interest within a sample is provided. The system includes a desorber and an analysis device. The desorber is configured to release a vapor from the sample, wherein the desorber includes an inlet configured to receive the sample, a heating element configured to release the vapor from the sample, and an active cooling element configured to cool the desorber. The analysis device is configured to screen the vapor for the substance of interest

DRAWINGS

These and other features, aspects, and advantages of the present disclosure will become better understood when the following detailed description is read with reference to the accompanying drawings in which like characters represent like parts throughout the drawings, wherein.

Figure 1:
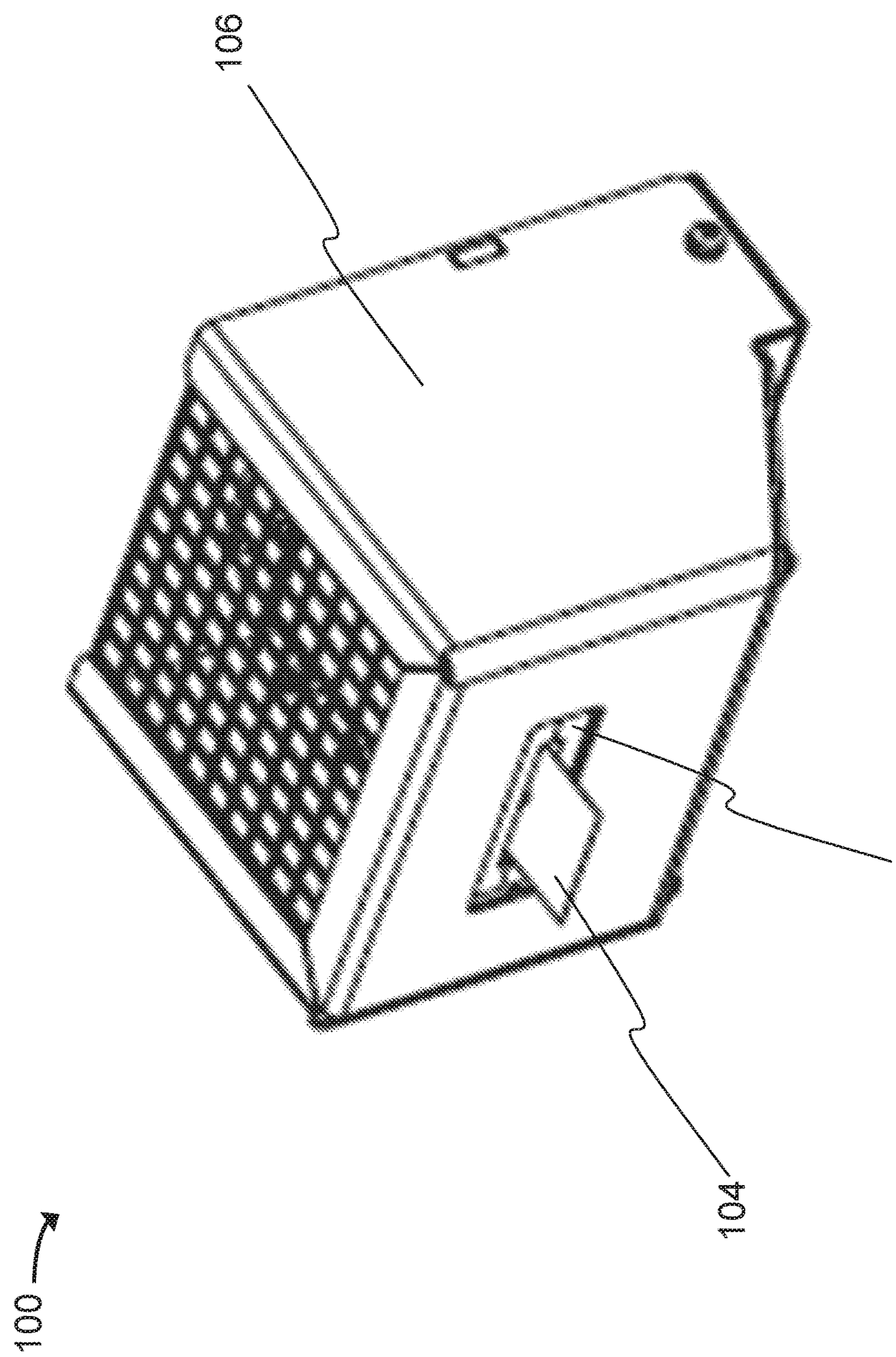
FIG. 1 is a perspective diagram of an exemplary desorber.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, a number of terms are referenced that have the following meanings.

The singular forms "a," "an," and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged. Such ranges are identified and include all the sub-ranges contained therein unless context or language indicates otherwise.

Conventional trace detection systems that require sample heating, such as in a desorber, may have limited sample throughput (i.e., the number of samples that can be analyzed in a given period of time) due to the time needed to cool the desorber enough to accept a subsequent sample. Different substances vaporize at different temperatures. Accordingly, depending on the phase and volatility of a substance of interest within a sample, the sample may require little to no heating (e.g., gaseous and/or high volatility substances), heating up to 100° C. (e.g., volatile explosives), heating up to 240° C. (e.g., conventional explosives), heating up to 380° C. (e.g., inorganic salts or homemade explosives), or heating above 380° C. (e.g., solid and/or low volatility substances). If the initial temperature of the desorber is too high when a sample is received at the inlet, the substance of interest in the sample will decompose and may not be detected at all, thus reducing system detection accuracy and performance. Providing an appropriately low initial temperature of the desorber is necessary to enable the trace detection system to accurately detect a wide range of illicit substances within a sample. Consequently, even when sample heating and detection steps occur rapidly, long lag times (e.g., 6 minutes or more) between samples due to slow desorber cooling significantly limits the throughput capabilities of the system.

It is realized herein it is important to actively and rapidly cool a desorber of a trace detection system for effective high throughput operation of the system. For example, an exemplary trace detection system used at an airport or other location where preferred time between samples is low and sample volume is high would require high throughput for detection of explosive substances. In addition, such a system would be required to accurately detect a wide range of substances. Accordingly, in order for a system to successfully and consistently vaporize various substances of interest at different temperatures within a reasonably short cycle time, an active cooling element for cooling the desorber is needed to reset the system for each subsequent sample.

Embodiments of the desorbers described herein enable active and rapid cooling of the desorbers. The desorber itself may have various forms and compositions for different systems and analysis, such as an internal cooling element, an external cooling element, or both. More specifically, the desorbers described herein incorporate at least one active cooling element configured to rapidly cool the desorber (e.g., by forced convection). In some embodiments, the desorber includes an internal cooling element configured to cool an internal portion of the desorber. In other embodiments, the desorber includes an external cooling element configured to cool an external portion of the desorber. In some embodiments, the desorber includes both internal and external cooling elements that may operate sequentially or simultaneously to achieve a desired target cooling rate and/or target temperature. An active cooling element may include fans, high volume pumps, liquid and gas coolants, thermal electric coolers, refrigeration cycles, and combinations thereof, for example. The active rapid desorber cooling described herein enables throughput cycle time to be substantially reduced, for example, down to 2 minutes or less, 1 minute or less, or 30 seconds or less. Accordingly, use of such specialized actively-cooled desorbers enhances sample throughput capabilities of a trace detection system.

Trace detection systems that embody the desorbers described herein may further include a control system, processor, or other computing device for operating the cooling element to enable rapid and active cooling of the desorber, such as, for example, simultaneous or sequential operation of internal and external cooling elements.

FIG. 1 is a perspective diagram of an exemplary desorber 100 for use in a trace detection system. Desorber 100 is configured to receive a sample at an inlet 102, such as on a sample on a trap 104. Desorber 100 includes a housing 106.

Figure 2:
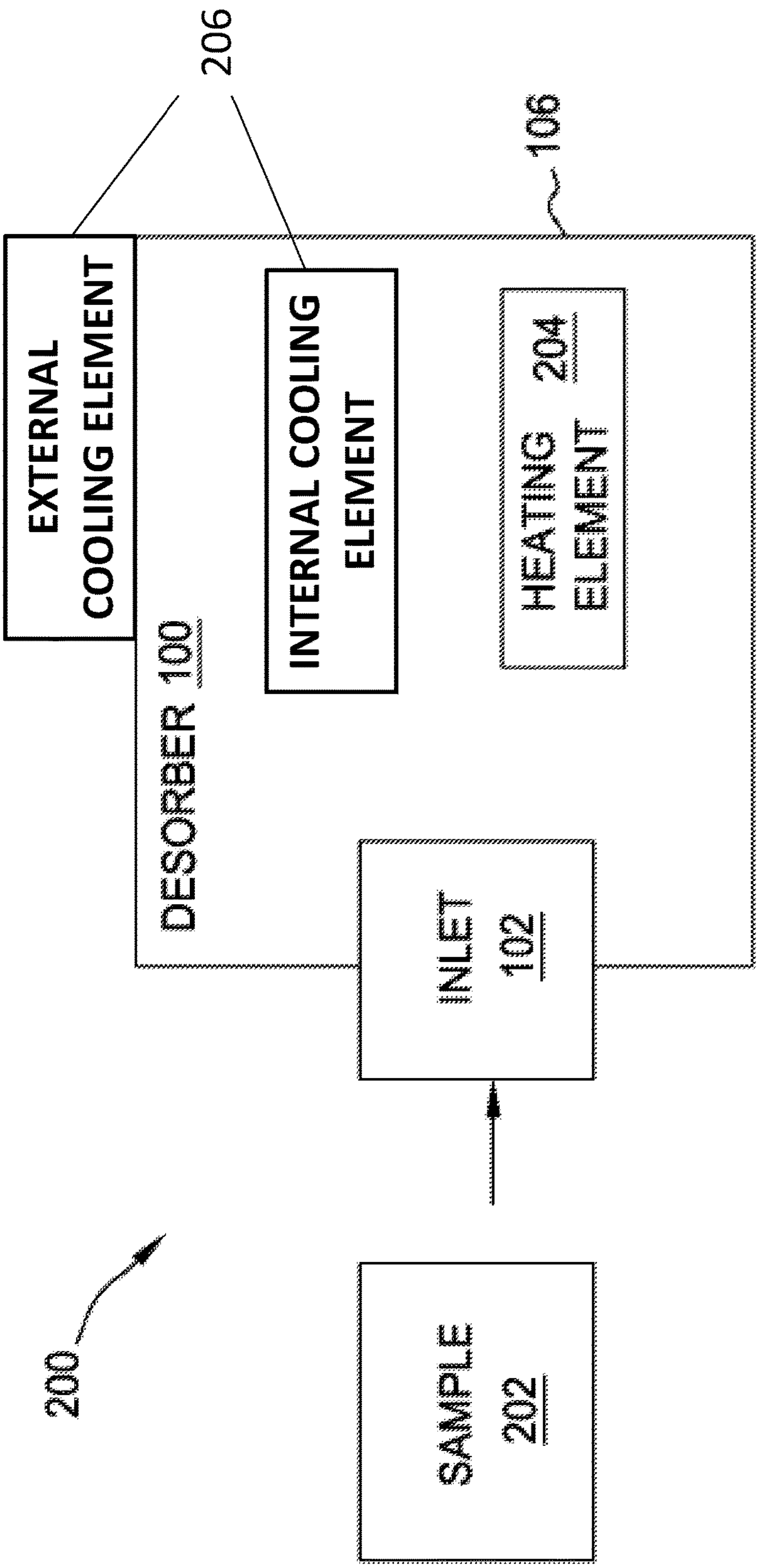
FIG. 2 is a block diagram of the desorber shown in FIG. 1.

FIG. 2 is a block diagram of desorber 100, shown in FIG. 1. Inlet 102 is configured to receive a sample 202. Sample 202 may be a gas phase, liquid phase, or solid phase sample. In some embodiments, sample 202 may be adsorbed on a trap (104, shown in FIG. 1) and received at inlet 102 via the trap 104. In some embodiments, inlet 102 may receive sample 202 via a transfer line (not shown) from another device, such as a pre-concentrator or other sample preparation or sample containment device. Desorber 100 also includes a heating element 204 configured to heat sample 202 to release a vapor for screening by an analysis device or detector (e.g., an ion mobility spectrometer). In some embodiments, heating element 204 may be a flash heater. In other embodiments, heating element 204 may be another suitable type of heater.

Desorber 100 further includes cooling element 206. Cooling element 206 may embody one or more active cooling elements configured to cool the desorber. For example, cooling element 206 may be configured to cool the desorber using forced convection. Cooling element 206 may be an internal cooling element configured to cool an internal portion of the desorber. An internal portion of the desorber 100 may include any portion in which sample 202 is contained, heated, and/or vaporized within the desorber 100. Cooling element 206 may be an external cooling element configured to cool an external portion of the desorber 100 and may, in some embodiments, be integrated into housing 106 of desorber 100. An external portion of the desorber 100 may include any portion outside of which sample 202 is contained, heated, and or vaporized. In some embodiments, desorber 100 may include both internal and external cooling elements 206. In certain embodiments when both internal and external cooling elements 206 are present, they may operate simultaneously or sequentially, depending on the cooling requirements for the desorber and desired sample cycle time, for example. Cooling element 206 may include at least one of a fan, a high-volume pump, a thermal electric cooler, a compressed gas, a liquid coolant, a gas coolant, an active refrigeration cycle, a compression refrigeration cycle, and an absorption refrigeration cycle.

As an example, a desorber 100 may include a high volume pump as the internal cooling element as well as a fan integrated into housing 106 as the external cooling element. Continuing with this example, the high volume pump and/or the fan may utilize un-treated or pre-treated (such as cooled and/or cleaned) ambient air. Alternatively, internal cooling using the high volume pump may utilize doped air, an inert gas, pre-treated air, or combinations thereof, for example.

In some embodiments, cooling element 206 may be a closed-loop, recirculating system. In certain embodiments when cooling element 206 is a recirculating system, desorber 100 may also include a heat exchanger (not shown). The heat exchanger may be coupled to (i.e., in thermal communication with) the active cooling element and configured to transfer heat from the active cooling element. For example, in embodiments where the active cooling element includes a liquid coolant, heat exchanger may transfer heat from the liquid coolant so that the coolant may be recirculated to cool the desorber within a single sample cycle or in a subsequent sample cycle.

Figure 3:
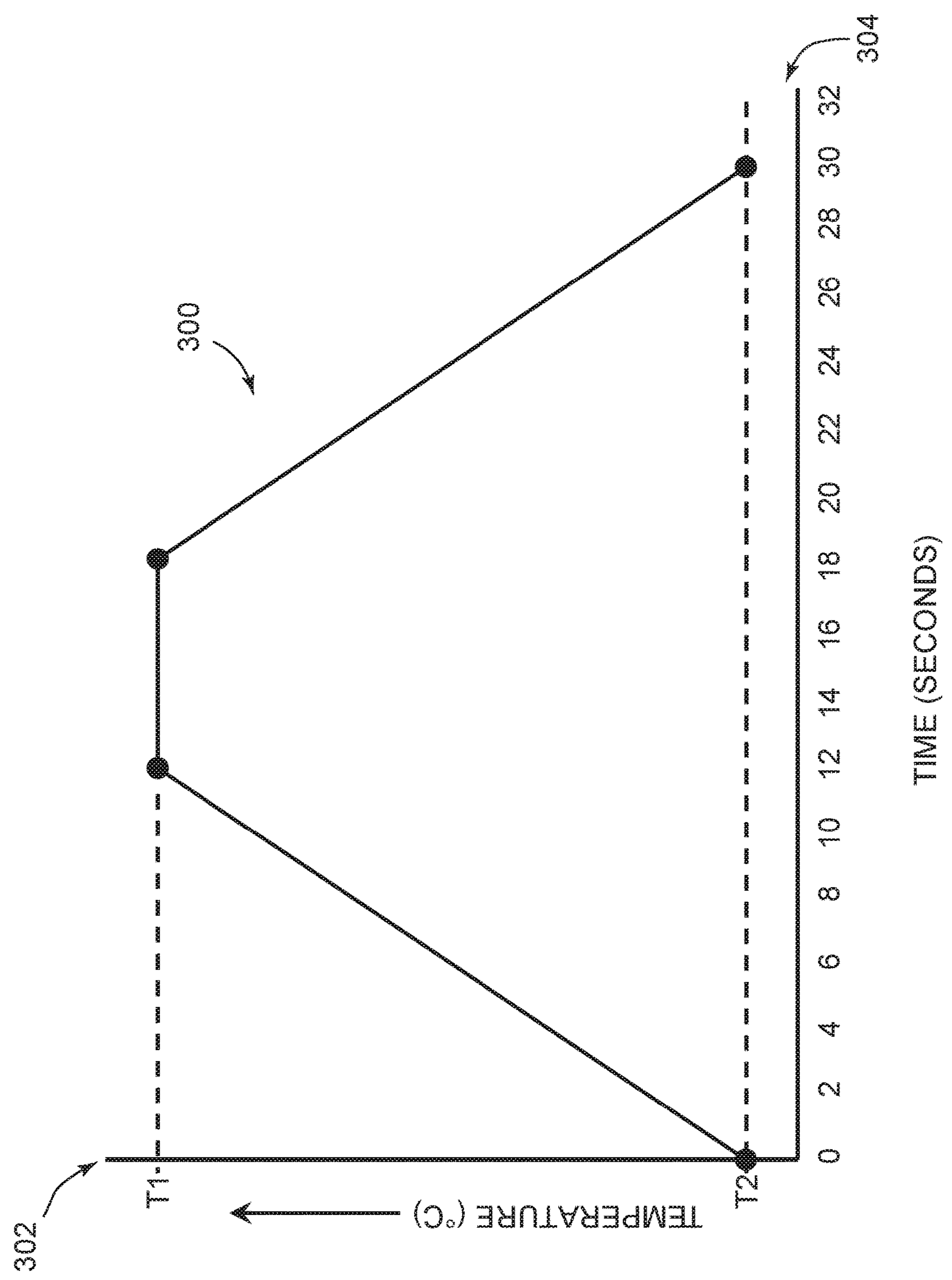
FIG. 3 is a graphical depiction of an exemplary desorber temperature profile.

FIG. 3 is a graphical depiction of an exemplary desorber temperature profile 300. The y-axis represents desorber temperature 302 in ° C. The x-axis represents sample cycle time 304 in seconds. At 0 seconds (where a time of 0 seconds is indicative of a sample being received at desorber inlet 102 and a sample cycle begins) the desorber temperature begins to increase until about 12 seconds when a target high temperature or first temperature T1 is reached. The temperature of desorber T1 is then held (maintained) at T1 from about 12 seconds until about 18 seconds, and the desorber 100 is then cooled down to a target low temperature or second temperature T2, from about 18 seconds until about 30 seconds. First temperature T1 is higher than second temperature T2. At some point before cooling of the desorber 100 begins, a vapor released during the heating of the desorber 100 (or, for example, as T1 is maintained between 12 and 18 seconds as shown in FIG. 3) is transferred from the desorber to an analysis device or detector (as discussed in greater detail below). In some embodiments, once the desorber 100 temperature has reached T2, the sample cycle ends and a new sample cycle may begin with a subsequent sample received at desorber inlet 102. While FIG. 3 shows T2 as the desorber temperature at both the beginning of the cycle (0 seconds) and the end of the cycle (about 30 seconds), note the initial temperature may or may not be equal to T2, depending on the embodiment. For example, once the desorber 100 is cooled to T2, the next sample cycle may begin (at 0 seconds) with an initial desorber temperature different than T2 (however an initial desorber temperature is still lower than T1). In some embodiments, the slope of temperature increase may be different than that shown in FIG. 3. Further, in some embodiments the slope of temperature decrease may be different than that shown in FIG. 3. Also note the overall cycle time (i.e., the cycle time necessary from to heat the desorber 100 from 0 seconds to T1 (including any time spent maintaining T1) followed by the time to cool the desorber down to T2) may be, for example, about 30 seconds or less (as shown in FIG. 3), about 60 seconds or less, or about 2 minutes or less, depending on the embodiment.

Figure 4:
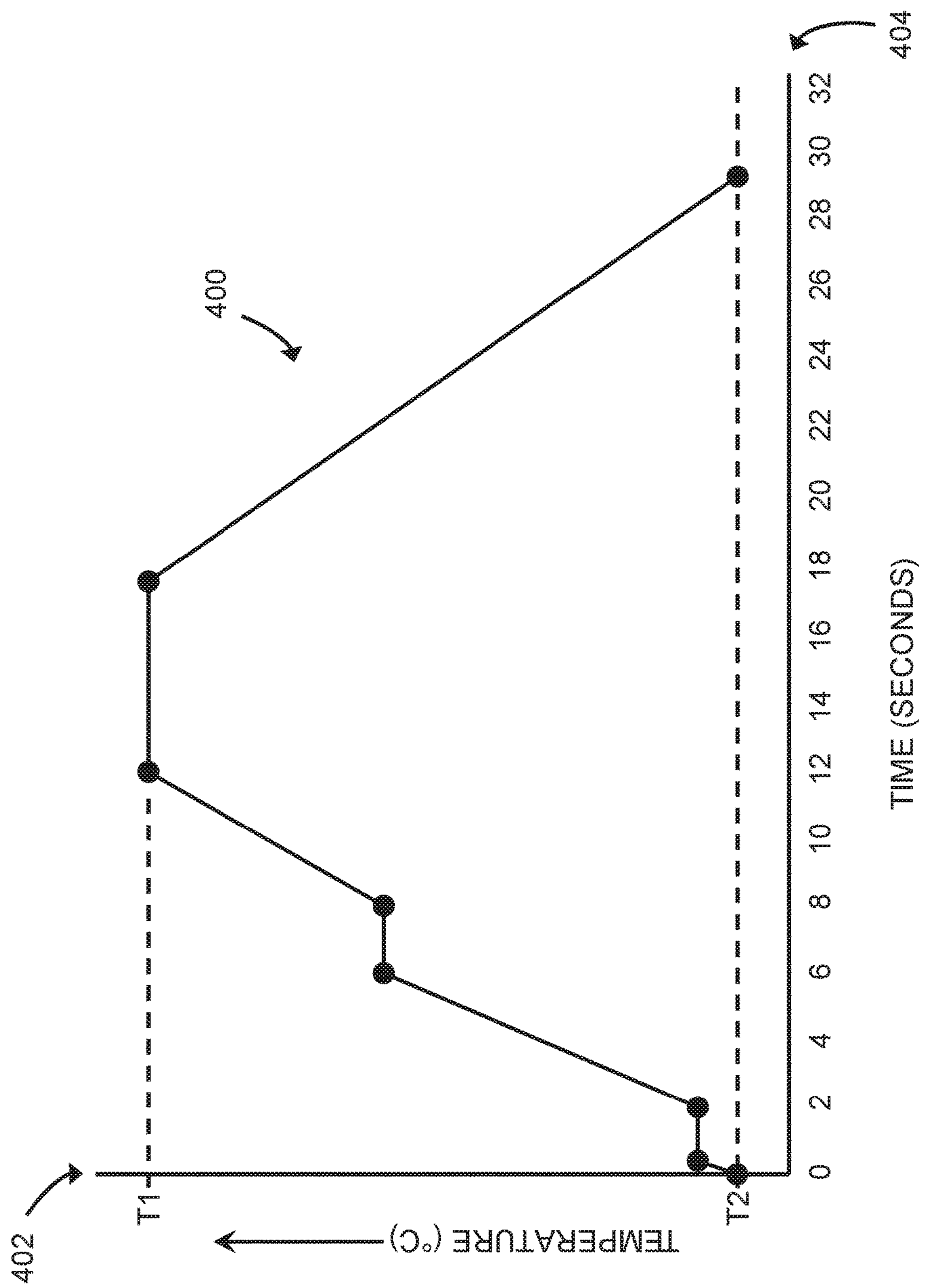
FIG. 4 is a graphical depiction of another exemplary desorber temperature profile.

FIG. 4 is a graphical depiction of another exemplary desorber temperature profile 400. The y-axis represents desorber temperature 402 in ° C. The x-axis represents sample cycle time 404 in seconds. Detection sensitivity for some substances of interest (e.g., some military and commercial explosives) may be improved by increasing a desorber temperature in stages, such as increasing the desorber temperature in stages between low and mid-range temperatures or between mid-range and high-range temperatures. In some embodiments, desorber 100 may be heated by heating element 204 in stages to reach a target high temperature or first temperature T1, as shown in FIG. 4. Depending on the embodiment, the temperature of desorber 100 may be held (maintained) at a certain temperature before continuing the temperature increase between stages up to T1. For instance, FIG. 4 shows an initial temperature increase between about 0 and 1 second (where a time of 0 seconds is indicative of a sample being received at desorber inlet 102 and a sample cycle begins), followed by maintaining a temperature between about 1 and 2 seconds. Continuing with the example shown in FIG. 4, the temperature of desorber 100 is again increased between a cycle time of about 2 seconds to about 6 seconds, followed by holding the temperature constant between about 6 seconds and about 8 seconds. The temperature of the desorber 100 is once again increased between about 8 seconds and about 12 seconds, at which time T1 (e.g., the target high temperature) is reached and subsequently maintained until about a cycle time of 18 seconds. In some embodiments, the slope of temperature increase may be different for different stages. Further, the slope of temperature decrease may be different than that shown in FIG. 4, depending on the embodiment. Note the number of stages used to reach T1 may be more or less than the number of stages shown in FIG. 4, depending on the embodiment. Also note the overall cycle time (i.e., the cycle time necessary from to heat the desorber 100 from 0 seconds to T1 (including any time spent maintaining a temperature between heating stages and maintaining T1) followed by the time to cool the desorber down to T2) may be, for example, about 30 seconds or less (as shown in FIG. 4), about 60 seconds or less, or about 2 minutes or less, depending on the embodiment.

Figure 5:
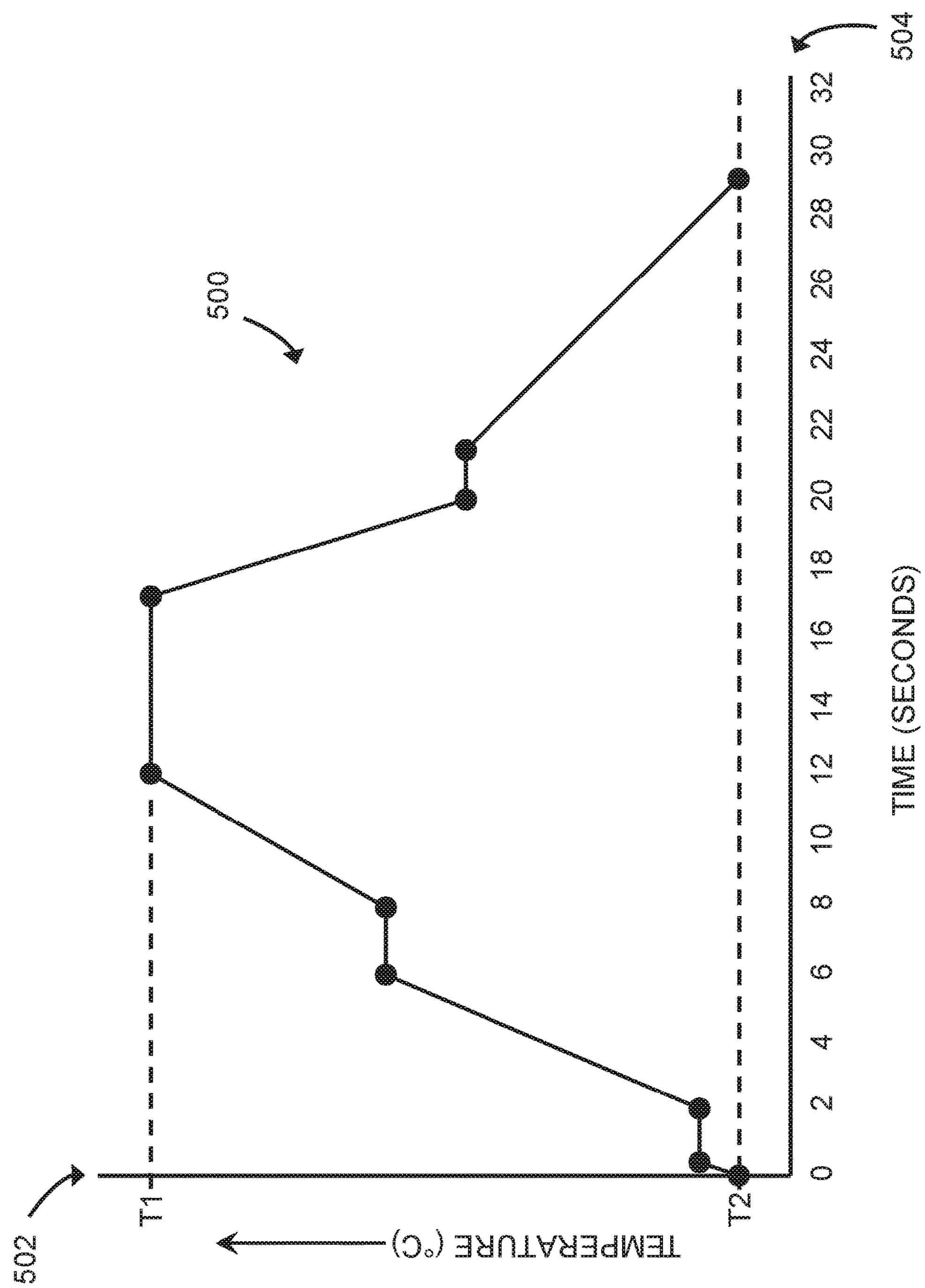
FIG. 5 is a graphical depiction of yet another exemplary desorber temperature profile.

FIG. 5 is a graphical depiction of yet another exemplary desorber temperature profile 500. The y-axis represents desorber temperature 502 in ° C. The x-axis represents sample cycle time 504 in seconds. In this example, desorber 100 temperature is increased in stages to reach T1 (as discussed above with respect to FIG. 4), and additionally decreased in stages to reach T2. Cooling desorber 100 in stages may improve overall cycle time efficiency, as well as consistency. In some embodiments, desorber 100 may be heated to temperature T1 in a single stage (as shown in FIG. 3), while cooling desorber to T2 is done using a plurality of stages. Desorber 100 may be cooled by cooling element 206 in stages to reach the target low temperature or second temperature T2, as shown in FIG. 5. Depending on the embodiment, the temperature of desorber 100 may be held (maintained) at a certain temperature between stages before continuing the temperature decrease down to T2. For instance, FIG. 5 shows that desorber 100 temperature reaches the target high temperature T1 at about 12 seconds and is maintained until about 18 seconds. At about 18 seconds, active cooling of desorber 100 begins. A first cooling stage occurs from about 18 seconds to about 20 seconds, and is followed by maintaining a temperature between about 20 seconds and about 22 seconds. Another cooling stage occurs between about 22 seconds and about 30 seconds, at which point the desorber 100 temperature has reached T2. In some embodiments, once the temperature of desorber 100 has reached T2, the sample cycle ends and a new sample cycle may begin with a subsequent sample received at desorber inlet 102. While FIG. 5 shows T2 as the desorber temperature at both the beginning of the cycle (0 seconds) and the end of the cycle (about 30 seconds), note the initial temperature may or may not be equal to T2, depending on the embodiment. For example, once the desorber 100 is cooled to T2, the next sample cycle may begin (at 0 seconds) with an initial desorber temperature different than T2 (however the initial desorber temperature at the beginning of a sample cycle is still less than T1). In some embodiments, the slope of temperature decrease may be different for different stages, and may be different than that shown in FIG. 5, depending on the embodiment. Note the number of stages used to cool the desorber from T1 to T2 may be more or less than the number of stages shown in FIG. 5, depending on the embodiment. Also note the overall cycle time (i.e., the cycle time necessary from to heat the desorber 100 from 0 seconds to T1 followed by the time to cool the desorber down to T2 (including any time spent maintaining a temperature between heating stages, maintaining T1, and maintaining a temperature between cooling stages)) may be, for example, about 30 seconds or less (as shown in FIG. 5), about 60 seconds or less, or about 2 minutes or less, depending on the embodiment.

Figure 6:
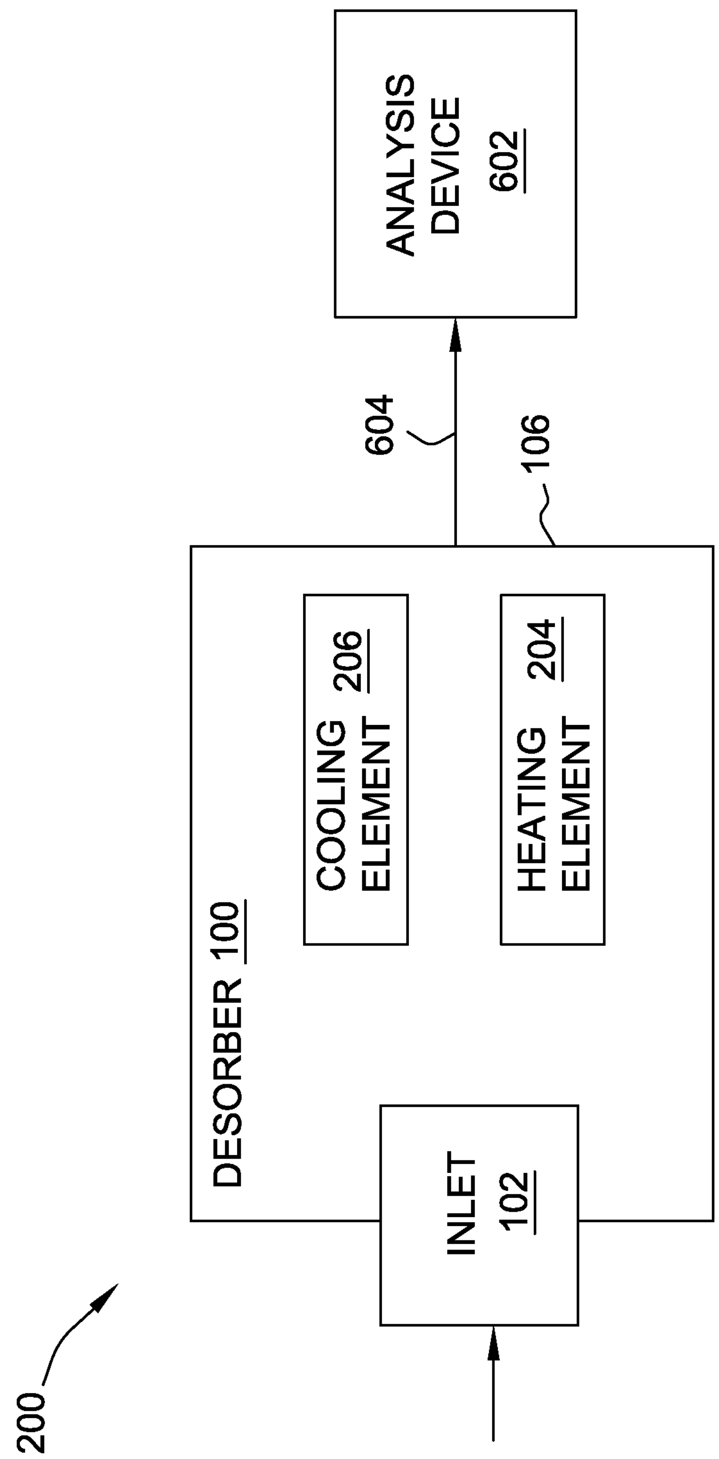
FIG. 6 is a block diagram of an exemplary trace detection system embodying the desorber shown in FIGS. 1 and 2.

FIG. 6 is a block diagram of an exemplary trace detection system 600 embodying desorber 100, shown in FIGS. 1 and 2. Desorber 100 includes inlet 102, heating element 204, and cooling element(s) 206. As described above, cooling element 206 may be an internal cooling element configured to cool an internal portion of the desorber 100. Cooling element 206 may additionally or alternatively include an external cooling element configured to cool an external portion of desorber 100, and may be integrated into housing 106 of the desorber 100. Trace detection system 600 further includes an analysis device 602 in flow communication with desorber 100. A vapor that has been released by heating a sample in desorber 100 is transferred from desorber 100 to analysis device 602 for screening. Arrow 604 indicates direction of vapor transfer from desorber 100 to analysis device 602. Analysis device 602 is configured to screen the vapor for a substance of interest. If present, the substance of interest is detected and identified by analysis device 602.

Substances of interest may include at least one of an explosive, an energetic material, a taggant, a narcotic, a pharmaceutical product, a toxin, a chemical warfare agent, a biological warfare agent, a pollutant, a pesticide, a toxic industrial chemical, a toxic industrial material, a homemade explosive, a pharmaceutical trace contaminant, a biomarker for medical applications, a chemical marker for medical applications, a biomarker for clinical hygienic applications, a chemical marker for clinical hygienic applications, a precursor thereof, a byproduct thereof, a metabolite thereof, and combinations thereof.

In trace detection system 600, analysis device 602 may include at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a raman spectrometer, a laser diode detector, a mass spectrometer (MS), an electron capture detector, a photoionization detector, a chemiluminescence-based detector, an electrochemical sensor, an infrared spectrometer, a lab-on-a-chip detector, and combinations thereof.

Figure 7:
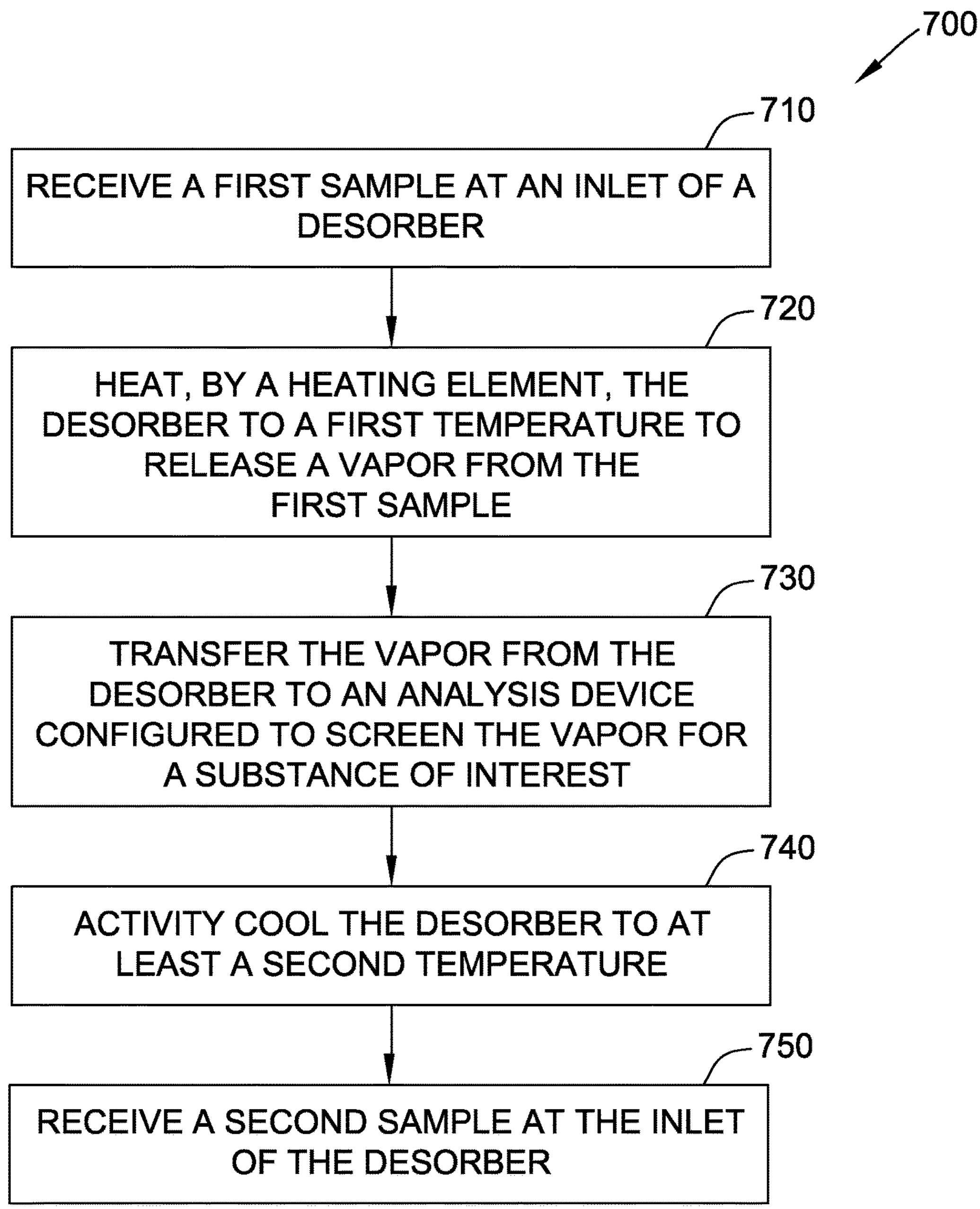
FIG. 7 is a flow diagram of an exemplary method of operating the trace detection system shown in FIG. 6.

FIG. 7 is a flow diagram of an exemplary method 700 of operating trace detection system 600 shown in FIG. 6, including desorber 100, shown in FIGS. 1 and 2. Method 700 includes receiving 710 a first sample (not shown) at an inlet 102 of a desorber 100, and heating 720, by a heating element 204, the desorber 100 to a first temperature to release a vapor from the first sample. Method 700 also includes transferring 730 the vapor from desorber 100 to analysis device 602. Analysis device 602 is configured to screen the vapor for a substance of interest. Method 700 further includes actively cooling 740 desorber 100 to at least a second temperature, and receiving 750 a second sample (not shown) at inlet 102 of desorber 100.

An exemplary technical effect of the methods, systems, and apparatus described herein includes at least one of: (a) increasing sample throughput capabilities of a trace detection system by significantly decreasing cycle times between samples; (b) preventing decomposition and/or loss of subsequent samples resulting from excessive initial desorber temperature; (c) improving analysis sensitivity through identification of substances of interest having widely varying vaporization temperatures; and (d) increasing overall system performance and efficiency by accurately and rapidly identifying a wide range of substances of interest.

Exemplary embodiments of methods, systems, and apparatus for desorbers are not limited to the specific embodiments described herein, but rather, components of systems and/or steps of the methods may be utilized independently and separately from other components and/or steps described herein. For example, the methods may also be used in combination with other non-conventional desorbers and trace detection systems, and are not limited to practice with only the systems and methods as described herein. Rather, the exemplary embodiment can be implemented and utilized in connection with many other applications, equipment, and systems that may benefit from increased efficiency, reduced operational cost, and reduced capital expenditure.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A desorber, comprising:
- a housing;
- an inlet integrated into the housing and configured to receive a sample;
- a heating element integrated into the housing and configured to generate heat that releases a vapor from the sample;
- an internal cooling element positioned within the housing and configured to cool the heating element; and
- an external cooling element integrated into the housing and configured to cool an external portion of the desorber, wherein the internal cooling element and the external cooling element are operable simultaneously or sequentially, and wherein the internal cooling element and external cooling element comprise at least one of a fan, a pump, a thermal electric cooler, a compression refrigeration cycle, or an absorption refrigeration cycle.

2. The desorber of claim 1, wherein the heating element is a flash heater.

3. A method of operating a trace detection system for detecting a substance of interest within a sample, wherein the trace detection system comprises a desorber having a housing, an inlet integrated into the housing, a heating element integrated into the housing, an internal cooling element positioned within the housing and configured to cool the heating element, and an external cooling element integrated into the housing and configured to cool an external portion of the desorber, and wherein the internal cooling element and external cooling element comprise at least one of a fan, a pump, a thermal electric cooler, a compression refrigeration cycle, or an absorption refrigeration cycle, the method comprising:
- receiving a first sample at the inlet;
- heating, by the heating element, the desorber to a first temperature to release a vapor from the first sample;
- transferring the vapor from the desorber to an analysis device configured to screen the vapor for the substance of interest;
- simultaneously using the external cooling element to actively cool the external portion of the desorber and using the internal cooling element to actively cool the heating element and an internal portion of the desorber to at least a second temperature; and receiving a second sample at the inlet.

4. The method of claim 3, wherein the first temperature is higher than the second temperature.

5. The method of claim 3, wherein heating the heating element to a first temperature comprises heating the heating element in a plurality of stages to reach the first temperature and vaporize the sample.

6. The method of claim 3, wherein actively cooling the heating element comprises cooling the heating element in a plurality of stages to reach the second temperature.

7. The method of claim 3, wherein a time between receiving the first sample and heating and then cooling the heating element to be ready for the second sample is 30 seconds or less.

8. The method of claim 3, wherein a time between receiving the first sample and heating and then cooling the heating element to be ready for the second sample is from 30-120 seconds.

9. A system for detecting a substance of interest within a sample, the system comprising:

a desorber comprising a housing, an inlet integrated into the housing and configured to receive the sample, a heating element integrated into the housing and configured to generate heat that releases a vapor from the sample, an internal cooling element positioned within the housing and configured to cool the heating element and an internal portion of the desorber, and an external cooling element integrated into the housing and configured to cool an external portion of the desorber, wherein the internal cooling element and the external cooling element are operable simultaneously or sequentially, and wherein the internal cooling element and external cooling element comprise at least one of a fan, a pump, a thermal electric cooler, a compression refrigeration cycle, or an absorption refrigeration cycle; and an analysis device configured to screen the vapor for the substance of interest.

10. The system of claim 9, wherein the substance of interest includes at least one of an explosive, an energetic material, a taggant, a narcotic, a pharmaceutical product, a toxin, a chemical warfare agent, a biological warfare agent, a pollutant, a pesticide, a toxic industrial chemical, a toxic industrial material, a homemade explosive, a pharmaceutical trace contaminant, a biomarker for medical applications, a chemical marker for medical applications, a biomarker for clinical hygienic applications, a chemical marker for clinical hygienic applications, a precursor thereof, a byproduct thereof, a metabolite thereof, or combinations thereof.

11. The system of claim 9, wherein the analysis device includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a raman spectrometer, a laser diode detector, a mass spectrometer (MS), an electron capture detector, a photoionization detector, a chemiluminescence-based detector, an electrochemical sensor, an infrared spectrometer, a lab-on-a-chip detector, or combinations thereof.

12. The system of claim 9, wherein the heating element is a flash heater.

13. The system of claim 9, wherein the inlet is configured to receive the sample in a solid phase, a liquid phase, a gas phase, or combinations thereof.

* * * * *